US008793727B2

(12) United States Patent
Serdiuk (10) Patent No.: US 8,793,727 B2
(45) Date of Patent: Jul. 29, 2014

(54) SYSTEM AND METHOD FOR SELECTING AUDIO/VIDEO CONTENT FOR PRESENTATION TO A USER IN RESPONSE TO MONITORED USER ACTIVITY

(75) Inventor: Dmytro Serdiuk, Kharkiv (UA)

(73) Assignee: EchoStar Ukraine, L.L.C., Kharkiv (UA)

( * ) Notice: Subject to any disclaimer, the term of this patent is extended or adjusted under 35 U.S.C. 154(b) by 0 days.

(21) Appl. No.: 13/514,017

(22) PCT Filed: Dec. 10, 2009

(86) PCT No.: PCT/UA2009/000066
§ 371 (c)(1),
(2), (4) Date: Jun. 5, 2012

(87) PCT Pub. No.: WO2011/071461
PCT Pub. Date: Jun. 16, 2011

(65) Prior Publication Data
US 2012/0254907 A1 Oct. 4, 2012

(51) Int. Cl.
*H04N 7/10* (2006.01)
*H04N 7/025* (2006.01)
*H04N 21/422* (2011.01)

(52) U.S. Cl.
CPC .............................. *H04N 21/42201* (2013.01)
USPC .......................................................... 725/36

(58) Field of Classification Search
USPC ....................................................... 725/9–14
See application file for complete search history.

(56) References Cited

U.S. PATENT DOCUMENTS

| 7,698,238 | B2 | 4/2010 | Barletta et al. | |
|---|---|---|---|---|
| 2002/0178440 | A1 | 11/2002 | Agnihotri et al. | |
| 2003/0063222 | A1* | 4/2003 | Creed et al. | 348/687 |
| 2003/0081834 | A1* | 5/2003 | Philomin et al. | 382/190 |
| 2003/0093784 | A1* | 5/2003 | Dimitrova et al. | 725/10 |
| 2003/0208335 | A1* | 11/2003 | Unuma et al. | 702/141 |
| 2004/0174431 | A1* | 9/2004 | Stienstra | 348/155 |
| 2005/0277814 | A1 | 12/2005 | Seo et al. | |

(Continued)

FOREIGN PATENT DOCUMENTS

WO    2009033187 A1    3/2009

OTHER PUBLICATIONS

European Patent Office "International Search Report" mailed Aug. 27, 2010; International Appln. No. PCT/UA2009/000066, filed Dec. 10, 2009.

(Continued)

*Primary Examiner* — Nathan Flynn
*Assistant Examiner* — Omar S Parra
(74) *Attorney, Agent, or Firm* — Ingrassia Fisher & Lorenz, P.C.

(57) ABSTRACT

A system for providing audio/video content to a user is disclosed. The system includes a set-top box device configured to provide audio/video content to a presentation device, and at least one sensor communicatively coupled to the set-top box device, the at least one sensor configured to provide sensor data to the set-top box device. The system also includes a sensor data processing module configured to process the sensor data to determine a probable activity type for the user, and a controller coupled to the sensor data processing module. The controller is configured to select particular audio/video content for playback at the presentation device, where the particular audio/video content is influenced by the probable activity type. Related operating methods are also provided.

20 Claims, 3 Drawing Sheets

(56) References Cited

U.S. PATENT DOCUMENTS

2006/0179450 A1 8/2006 Trappeniers et al.
2007/0033634 A1 2/2007 Leurs et al.
2007/0271580 A1 11/2007 Tischer et al.
2009/0195351 A1 8/2009 Takeda et al.

OTHER PUBLICATIONS

Oliver, Nuria et al. "PAPA: Physiology and Purpose-Aware Automatic Playlist Generation" ISMR 2006, [online] Oct. 12, 2006, XP007910448; Retrieved from the Internet: URL:http://ismir2006.ismir.net/PAPERS/ISMIR06162_Paper.pdf.

\* cited by examiner

SYSTEM AND METHOD FOR SELECTING AUDIO/VIDEO CONTENT FOR PRESENTATION TO A USER IN RESPONSE TO MONITORED USER ACTIVITY

CROSS-REFERENCES TO RELATED APPLICATIONS

This Application claims priority to International Application No. PCT/UA2009/000066, filed Dec. 10, 2009.

TECHNICAL FIELD

Embodiments of the subject matter described herein relate generally to content delivery systems such as satellite video systems. More particularly, embodiments of the subject matter relate to a video services receiver (such as a set-top box) that provides audio/video content that is appropriate for a detected level of physical activity of the user.

BACKGROUND

Most television viewers now receive their video signals through a content aggregator such as a cable or satellite television provider. In a typical scenario, encoded audio/video signals are sent via a cable or wireless data link to the viewer's home, where the signals are ultimately decoded in a set-top box or other consumer device. The decoded signals can then be viewed on a television or other appropriate display as desired by the viewer. Many viewers watch video programming or listen to audio delivered via a set-top box while they are exercising, working out, stretching, doing yoga, or performing other types of physical activities. In a typical scenario, the user will manually select a desired video or audio program, tune the set-top box to the chosen program, and then begin or continue with the physical activity. It may be desirable to select a relatively dynamic, exciting, fast-paced and/or loud program while performing certain types of exercise (e.g., an aggressive aerobic routine, a fast-paced exercise cycle stage, or a kickboxing workout). Conversely, it may be desirable to select a relatively calm, quiet, soothing, and/or slow-paced program while performing other types of exercise (e.g., yoga, stretching, mediation, tai chi, or the like). Traversing a programming guide or changing programs during an exercise regimen, however, can be inconvenient, disruptive, and difficult to achieve.

BRIEF SUMMARY

An exemplary embodiment of a method of presenting audio/video content to a user is provided here. The method monitors, with a set-top box device, a physical activity level of the user, and determines a probable activity type based upon the monitored physical activity level. The method continues by selecting, with the set-top box device, particular audio/video content that is correlated to the probable activity type. The method then provides the particular audio/video content to a presentation device.

Also provided is an exemplary embodiment of a method of controlling presentation of content to a user. This method begins by obtaining, at a set-top box device, sensor data that is indicative of physical activity of the user. The method continues by processing the sensor data to determine a probable activity type for the user, identifying a category of audio/video content that is correlated to the probable activity type, and selecting, for playback at a presentation device, particular audio/video content that is included in the category.

An exemplary embodiment of a system for providing audio/video content to a user is also provided. The system includes a set-top box device configured to provide audio/video content to a presentation device, and at least one sensor communicatively coupled to the set-top box device, where the at least one sensor is configured to provide sensor data to the set-top box device. The system also includes a sensor data processing module configured to process the sensor data to determine a probable activity type for the user, and a controller coupled to the sensor data processing module. The controller is configured to select particular audio/video content for playback at the presentation device, wherein the particular audio/video content is influenced by the probable activity type.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. Moreover, it should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

The techniques and technology described herein can be employed in the context of a video delivery system such as a cable television system, a satellite television system, a computer-based content delivery system, or the like. The disclosed subject matter relates to certain features and functions of a video services receiver (such as a set-top box). In particular, the set-top box is suitably configured to gather and analyze sensor data to monitor, determine, or estimate the current physical activity level of the user and/or the exercise type being performed by the user. Depending upon the probable activity type, the set-top box (or a remote system or component) selects appropriate audio/video content that matches well with that activity type.

Figure 1:
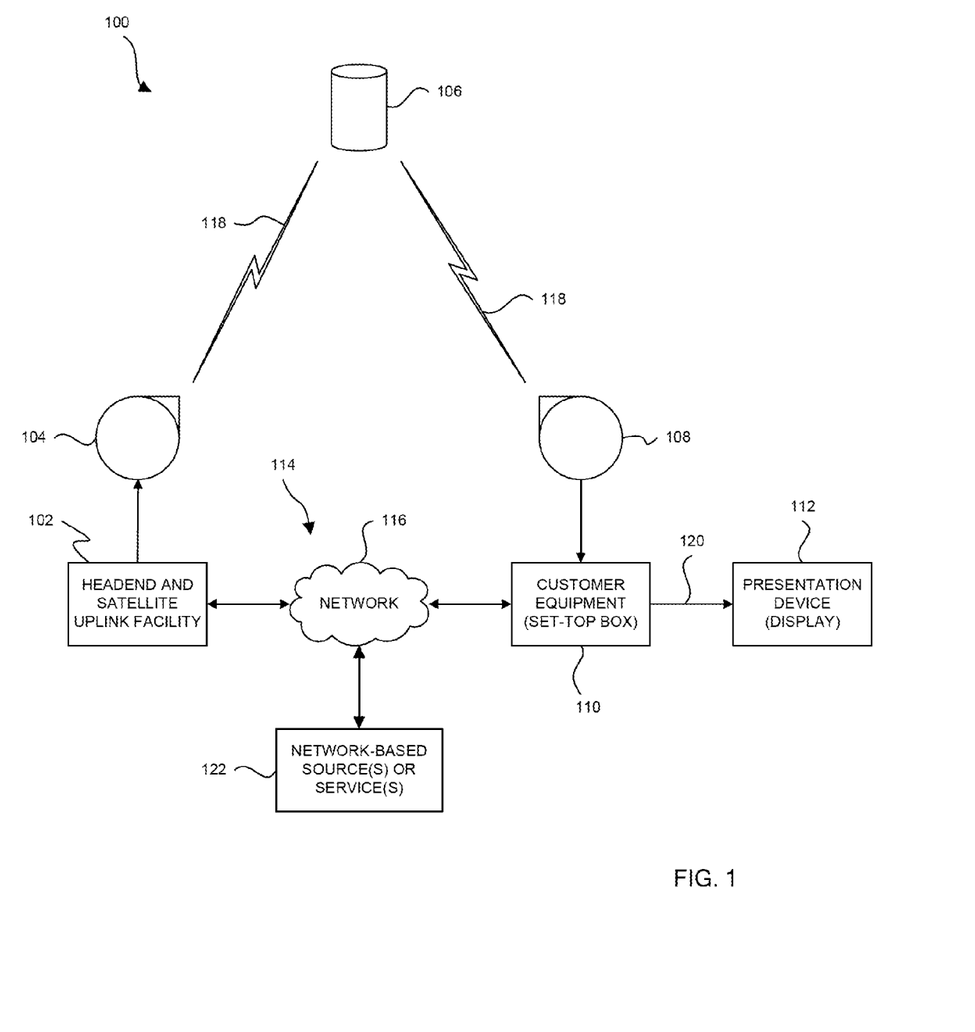
FIG. 1 is a schematic representation of an embodiment of a video services broadcasting system.

Turning now to the drawings, FIG. 1 is a schematic representation of an embodiment of a video services broadcasting system 100 that is suitably configured to support the techniques and methodologies described below. The system 100 (which has been simplified for purposes of illustration) generally includes, without limitation: a data center 102; an uplink transmit antenna 104; a satellite 106; a downlink receive antenna 108; a video services receiver 110 or other customer equipment; and a presentation device 112 (such as a display, a monitor, a television, audio equipment, or the like). In certain embodiments, the data center 102 communicates with the video services receiver 110 via a back-channel connection 114, which may be established through one or more data communication networks 116. For the sake of brevity, conventional techniques related to satellite communication systems, satellite broadcasting systems, DVB systems, data transmission, signaling, network control, and other functional aspects of the systems (and the individual operating components of the systems) may not be described in detail herein.

The data center 102 may be deployed as a headend facility and/or a satellite uplink facility for the system 100. The data center 102 generally functions to control content and data sent over a high-bandwidth link 118 to any number of downlink receive components (only one downlink receive antenna 108, corresponding to one customer, is shown in FIG. 1). In the embodiment shown in FIG. 1, the high-bandwidth link 118 is a direct broadcast satellite (DBS) link that is relayed by the satellite 106, although equivalent embodiments could implement the high-bandwidth link 118 as any sort of cable, terrestrial wireless and/or other communication link as desired.

The data center 102 includes one or more conventional data processing systems or architectures that are capable of producing signals that are transmitted via the high-bandwidth link 118. In various embodiments, the data center 102 represents a satellite or other content distribution center having: a data control system for controlling content, signaling information, blackout information, and other data; and an uplink control system for transmitting content, signaling information, blackout information, and other data using the high-bandwidth link 118. These systems may be geographically, physically and/or logically arranged in any manner, with data control and uplink control being combined or separated as desired.

The uplink control system used by the system 100 is any sort of data processing and/or control system that is able to direct the transmission of data on the high-bandwidth link 118 in any manner. In the exemplary embodiment illustrated in FIG. 1, the uplink transmit antenna 104 is able to transmit data to the satellite 106, which in turn uses an appropriate transponder for repeated transmission to the downlink receive antenna 108. Under normal operating conditions, the satellite 106 transmits content, signaling data, blackout information, and other data to the downlink receive antenna 108, using the high-bandwidth link 118. In practical embodiments, the downlink receive antenna 108 represents the customer's satellite dish, which is coupled to the video services receiver 110.

The video services receiver 110 can be realized as any device, system or logic capable of receiving signals via the high-bandwidth link 118 and the downlink receive antenna 108, and capable of providing demodulated content to a customer via the presentation device 112. The presentation device 112 may be implemented as, or include, without limitation: a television set; a monitor; a computer display; or any suitable customer appliance with compatible display and/or sound capabilities. In various embodiments, the video services receiver 110 is a conventional set-top box commonly used with DBS or cable television distribution systems. In other embodiments, however, the functionality of the video services receiver 110 may be commonly housed within the presentation device 112. In still other embodiments, the video services receiver 110 is a portable device that may be transportable with or without the presentation device 112. The video services receiver 110 may also be suitably configured to support broadcast television reception, video game playing, personal video recording and/or other features as desired.

During typical operation, the video services receiver 110 receives programming (broadcast events), signaling information, and/or other data via the high-bandwidth link 118. The video services receiver 110 then demodulates, decompresses, descrambles, and/or otherwise processes the received digital data, and then converts the received data to suitably formatted video signals 120 that can be rendered for viewing by the customer on the presentation device 112. Additional features and functions of the video services receiver 110 are described below with reference to FIG. 2 and FIG. 3.

Certain embodiments of the system 100 may also include or cooperate with any number of network-based content sources and/or any number of network-based services (e.g., content aggregation services, content delivery services, Internet radio stations, content providers, digital media vendors, or the like). In this regard, FIG. 1 depicts one block that represents these network-based sources or services 122. These network-based sources or services 122 can provide access to media or audio/video content available via the networks 116 (for example, the Internet). If the video services receiver 110 is web-enabled, then it can present web-based audio/video content from the network-based sources or services 122, as is well understood. For example, certain embodiments of the video services receiver 110 could utilize uniform resource locators (URLs) that point to content managed, provided, or otherwise accessible through the network-based sources or services 122. In this regard, the video services receiver 110 could be suitably configured to present streaming media using the presentation device 112.

In certain embodiments, one or more of the network-based sources or services 122 may be configured to process sensor data (and/or pre-processed data that is derived from or otherwise based upon raw sensor data) that is collected at the video services receiver 110 and/or at the presentation device 112. In such embodiments, a network-based source or service 122 could analyze the raw or pre-processed sensor data, determine a probable activity type associated with the monitored user, and then take appropriate actions. For example, the network-based source or services 122 could select a category, classification, or genre of audio/video content that is correlated to the probable activity type, and then select particular audio/video content or programs from the selected category, classification, or genre. This aspect of the system 100 is described in more detail below with reference to FIG. 2 and FIG. 3.

Figure 2:
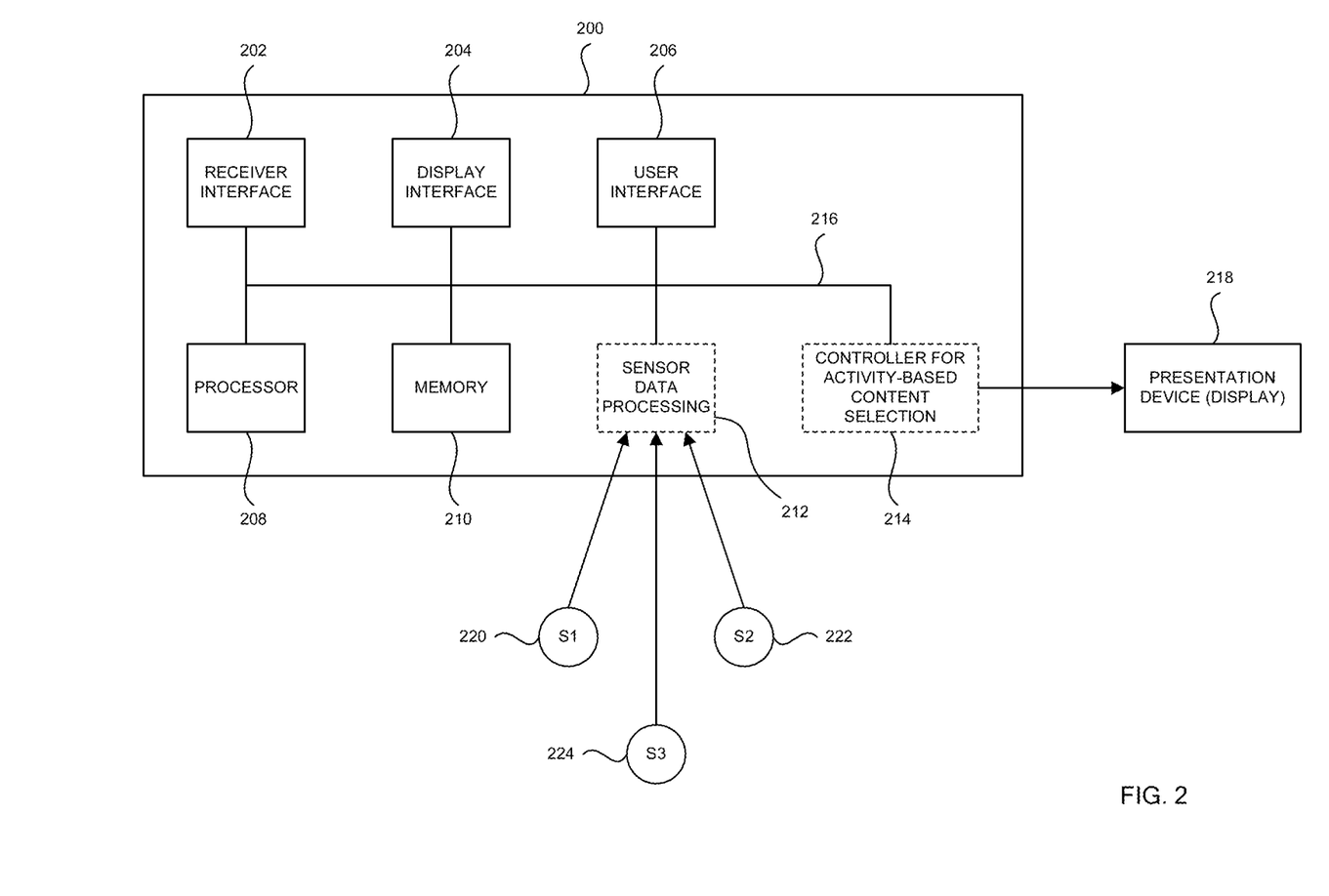
FIG. 2 is a schematic representation of an embodiment of a set-top box device, which is suitable for use in the video services broadcasting system shown in FIG. 1.

As mentioned above, the video services receiver 110 could be realized as a set-top box device. In this regard, FIG. 2 is a schematic representation of an exemplary embodiment of a set-top box device 200 suitable for use in a video services broadcasting system, such as the system 100 shown in FIG. 1. The set-top box device 200 is configured to receive video content, and to provide the video content to the customer on an appropriate presentation device, such as the presentation device 112 shown in FIG. 1. This embodiment of the set-top box device 200 generally includes, without limitation: a receiver interface 202; a display interface 204; a user interface 206; at least one processor 208; at least one memory element 210; a sensor data processing module 212; and a controller 214 that controls the selection of audio/video content in a manner that is influenced by the monitored activity level of the user. In some embodiments, the controller 214 is also suitably configured to control certain presentation-related parameters, characteristics, and/or features (described in more detail below). These components, modules, and elements may be coupled together as needed for purposes of interaction and communication using, for example, an appropriate interconnect arrangement or architecture 216. In practice, the set-top box device 200 will include additional elements and features that support conventional functions and operations.

As explained above with reference to FIG. 1, the set-top box device 200 may be suitably arranged to cooperate with a presentation device 218, which typically includes or is coupled to a display. In other words, the set-top box device 200 is configured to provide audio/video programs or services to the presentation device 218, as is well understood. In some embodiments, the set-top box device 200 is coupled to the presentation device 218 using a suitable data communication specification, standard, or protocol (such as, for example, the home networking protocols set forth by the Digital Living Network Alliance). For the illustrated embodiment, the display interface 204 is suitably configured to facilitate rendering of video and/or still images on the presentation device 218. Moreover, the controller 214 may be communicatively coupled to the presentation device 218 in an appropriate manner to enable it to adjust at least one operating characteristic, parameter, or feature of the presentation device 218 as needed.

In certain embodiments, the set-top box device 200 can be deployed as part of a system for providing audio/video content to a user, where that system also includes the presentation device 218 and at least one sensor configured to provide sensor data to the set-top box device 200. Accordingly, the embodiment depicted in FIG. 2 also includes a first sensor 220, a second sensor 222, and a third sensor 224, each being communicatively coupled to the set-top box device 200. In practice, these sensors can provide their respective sensor data to the sensor data processing module 212 so that the sensor data can be processed, analyzed, and otherwise handled in the manner described in more detail below.

The receiver interface 202 is coupled to the customer's satellite antenna, and the receiver interface 202 is suitably configured to receive and perform front end processing on signals transmitted by satellite transponders. In this regard, the receiver interface 202 can receive data associated with any number of services. The receiver interface 202 may leverage conventional design concepts that need not be described in detail here. The display interface 204 is coupled to at least the presentation device 218 (and possibly others) at the customer site. The display interface 204 represents the hardware, software, firmware, and processing logic that are utilized to render graphics, images, video, and other visual indicia on the customer's display. The display interface 204 may leverage conventional design concepts that need not be described in detail here. The user interface 206 may include one or more elements, components, or features that accommodate user inputs and/or that provide feedback to the user. For example, the user interface 206 may include, without limitation: keys; buttons; switches; a keyboard; a touchpad; a touch screen; a mouse or equivalent pointing device; indicator lights; or the like.

The processor 208 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. In particular, the processor 208 may be realized as a microprocessor, a controller, a microcontroller, or a state machine. Moreover, the processor 208 may be implemented as a combination of computing devices, e.g., a combination of a digital signal processor and a microprocessor, a plurality of microprocessors, one or more microprocessors in conjunction with a digital signal processor core, or any other such configuration. As described in more detail below, the processor 208 (cooperating with the sensor data processing module 212 and the controller 214) may be adapted to change certain presentation characteristics and/or change the current audio/video content based upon the detected level of user physical activity.

The memory element 210 may be realized as RAM memory, flash memory, EPROM memory, EEPROM memory, registers, a hard disk, a removable disk, or any other form of storage medium known in the art. In this regard, the memory element 210 can be coupled to the processor 208 such that the processor 208 can read information from, and write information to, the memory element 210. In the alternative, the memory element 210 may be integral to the processor 208. As an example, the processor 208 and the memory element 210 may reside in a suitably designed ASIC. In practice, the memory element 210 can be utilized to store and maintain information, tables, and data as needed to support the user activity monitoring techniques described herein.

The sensor data processing module 212 may be implemented as part of the processor 208 or as a separate logical component. For instance, the sensor data processing module 212 could be implemented in a subsystem, device, or component other than the set-top box device 200 (such as a network-based source or service). Indeed, in certain embodiments the sensor data processing module 212 is maintained by a network-based content provider that communicates with the set-top box device 200. For this reason, the sensor data processing module 212 is depicted in dashed lines in FIG. 2.

The sensor data processing module 212 receives or obtains the sensor data (or data derived from the sensor data), and processes the sensor data in an appropriate manner to determine a probable or likely physical activity type of the user. Therefore, the configuration, design, and functionality of the sensor data processing module 212 can differ from one embodiment to another, depending upon the number and/or types of sensors deployed with the set-top box device 200. For example, if a microphone is used to detect breathing (respiration) sounds, then the sensor data processing module 212 will be suitably configured to analyze captured sound data. As another example, if a camera is used as one of the sensors, then the sensor data processing module 212 will include image processing capabilities that enable analysis of captured still or video images. In practical implementations, therefore, the sensor data processing module 212 could include or be associated with one or more software applications that are written to support the desired amount and level of sensor data processing.

The controller 214 may be implemented as part of the processor 208 or as a separate logical component. For instance, the controller 214 could be implemented in a subsystem, device, or component other than the set-top box device 200 (such as a network-based source or service). Indeed, in certain embodiments the controller 214 is maintained by a network-based content provider that communicates with the set-top box device 200. For this reason, the controller 214 is depicted in dashed lines in FIG. 2.

The controller 214 may be operationally coupled to the sensor data processing module 212 to enable it to respond to certain tasks performed by the sensor data processing module 212. In this regard, the controller 214 can be suitably configured to take appropriate action when the sensor data processing module 212 determines that the user is engaging in one form of physical activity or exercise (e.g., yoga), and to take different action when the sensor data processing module 212 determines that the user is engaging in a different form of physical activity or exercise (e.g., aggressive calisthenics). In certain embodiments, the controller 214 identifies a category of audio/video content that is correlated to a detected user activity type. In such embodiments, the controller 214 could select particular audio/video content for playback at the presentation device 218, where the selected audio/video content is appropriate for the current type or level of physical activity, which has been detected or determined by the system.

Although FIG. 2 depicts three sensors 220, 222, and 224 for this exemplary embodiment, any number of sensors (including only one) could be deployed with an embodiment of the set-top box device 200. A given sensor may include, cooperate with, or be realized as any of the following sensor types, without limitation: a motion detector; an accelerometer, a pedometer; a perspiration meter; a video camera; a still camera; a microphone; a sound meter; a physiological characteristic sensor; a thermometer; a clock; or the like. It should be appreciated that other sensor types and configurations could be employed if so desired. Although not shown in FIG. 2, any given sensor could be implemented as an integral component of the set-top box device 200. In other words, a sensor could be considered to be part of the set-top box device 200 or otherwise attached to the set-top box device 200. As shown in FIG. 2, however, the sensors may be realized as separate physical devices or components that are physically and/or wirelessly coupled to the set-top box device 200. In this regard, a sensor could be connected via cables or wires to accommodate data transfer to the set-top box device 200. In alternate embodiments, a sensor could be realized as a standalone device or component, and the set-top box device 200 and that sensor could be compatibly configured to accommodate wireless transmission of sensor data.

A motion detector could employ infrared, laser, or sonic interrogation techniques to scan the environment for movement or motion. Such a motion detector would preferably (but need not be) positioned near the viewing or listening area such that the user is within the range of the motion detector. An accelerometer may be worn or carried by the user, and it could be used to measure or derive acceleration information, velocity information, body movement information, body orientation information, body posture information, body positioning information, etc. A pedometer may be worn or carried by the user to measure the number of steps (or other gestures) performed over a particular period of time, to estimate a distance traveled (actual or simulated), or the like. A perspiration meter could be worn or carried by the user to obtain sensor data related to the amount of perspiration measured during a particular period of time, the amount of water or electrolytes lost during a particular period of time, etc.

A still or video camera could be used to provide digital image data to the set-top box device 200. The image data could be processed to detect the presence of the user and to determine whether the user's movements are indicative of relatively high physical activity, relatively low physical activity, relatively intermediate physical activity, or the like. In certain embodiments, the image data could also be used to analyze certain visual cues that might be indicative of the level or type of physical activity. For example, the system may be suitably configured to detect visual traits or characteristics of the user that indicate an overworked state, a calm state, a relaxed state, a tired state, or the like. If used, cameras would preferably (but need not be) positioned near the viewing or listening area, and within image capturing range of the user. A microphone could be used to monitor for background noise, voices, breathing patterns, or other sounds that might be indicative of physical activity. If used, a microphone would preferably (but need not be) positioned near the viewing or listening area, and one could be located near or integrated into the set-top box device 200. In some embodiments, it might be desirable to locate a microphone near the user, such that breathing and other sounds can be detected easily. Similarly, a sound meter could be used to measure sound pressure levels near the set-top box device 200. If used, a sound meter would preferably (but need not be) positioned near the viewing or listening area, or near the user.

In certain embodiments, one or more physiological characteristic sensors could be employed by the system. As used here, a physiological characteristic sensor is any sensor, detector, device, or component that is configured to measure a physiologic characteristic of a person. For example, and without limitation, a physiological characteristic sensor could be: a heart rate monitor that obtains user heart rate data; a pedometer or accelerometer that obtains user motion data; a breathing or respiration monitor that obtains user respiration data; a body thermometer that obtains user temperature data; an electrocardiogram (ECG) device; an electroencephalogram (EEG) device; a blood glucose sensor or meter; or the like.

Figure 3:
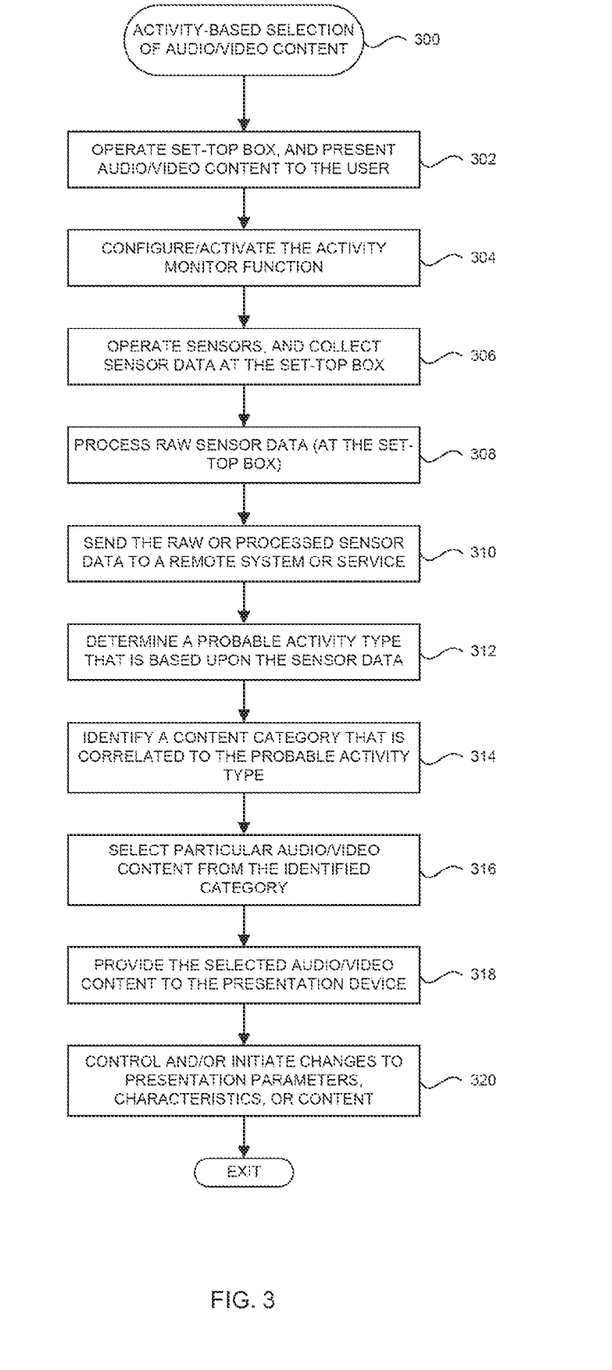
FIG. 3 is a flow chart that illustrates an exemplary embodiment of an activity-based audio/video content selection process.

A set-top box device configured in the manner described above can be utilized to monitor physical activity of the user and, in response thereto, provide appropriate audio/video content to a presentation device (the content can be automatically chosen for suitability with the level or type of physical activity). In this regard, FIG. 3 is a flow chart that illustrates an exemplary embodiment of an activity-based audio/video content selection process 300, which may be performed by an appropriately configured set-top box device. The various tasks performed in connection with process 300 may be performed by software, hardware, firmware, or any combination thereof. For illustrative purposes, the following description of process 300 may refer to elements mentioned above in connection with FIG. 1 and FIG. 2. In practice, portions of process 300 may be performed by different elements of the described system, e.g., a sensor, the set-top box, or a network-based system or component other than the set-top box device. It should be appreciated that process 300 may include any number of additional or alternative tasks, the tasks shown in FIG. 3 need not be performed in the illustrated order, and process 300 may be incorporated into a more comprehensive procedure or process having additional functionality not described in detail herein. Moreover, one or more of the illustrated tasks for process 300 could be omitted from an embodiment as long as the intended functionality remains intact.

The illustrated embodiment of process 300 begins by operating the set-top box device and, under certain circumstances, by presenting audio/video content to the user (task 302). The audio/video content may include audio only, video only, still images only, or any combination thereof. The audio/video content may be provided as a service by a cable or satellite service provider, as a downloaded or streaming media file by a web-based service, by a digital video recorder device coupled to the set-top box device, by a digital video recorder feature that is embedded or integrated in the set-top box device, or by other suitable means. Although not always required, this embodiment assumes that the user has the ability to configure, initialize, or otherwise start the activity monitoring function (task 304) of the set-top box device. In such an embodiment, the activity monitoring feature must be activated for it to be effective. This type of arrangement might be desirable in a deployment that uses body-worn or body-carried sensors. In alternate embodiments, the activity monitoring feature could be active by default, or it could always be active and running in the background. If the system cooperates with a network-based source or service (as described below for certain embodiments), then task 302 may also involve a user authentication procedure carried out between the set-top box device (or, equivalently, the user) and the network-based source or service. Such an authentication procedure prepares the network-based source or service for the remainder of the process 300.

Assuming that the activity monitor function is active, the process 300 operates the sensors to obtain or collect the corresponding sensor data at the set-top box device (task 306). As mentioned above, a sensor could provide its sensor data to the set-top box device using a tangible data communication link and/or using a wireless data communication link. The sensor data (from any individual sensor or collectively from any number of sensors) is indicative of, associated with, or otherwise related to user activity in some way. For example, the sensor data may include, without limitation: user motion data; user acceleration data; user velocity data; user posture data; user body position data; user heart rate data; user respiration data; user sound data; user perspiration data; user physiological characteristic data; user temperature data; or the like. In practice, the sensor data will vary with different levels, amounts, or types of physical activity. Thus, if at least some of the sensor data indicates a high amount of user motion, high acceleration of the user (or high acceleration of certain body parts), or high velocity of the user (or high velocity of certain body parts), then that sensor data would suggest a relatively high amount of physical activity. As another example, the user posture data and/or the user body position data might be indicative of certain types or forms of exercise, such as meditation, yoga posing, riding a stationary bicycle, etc. Some physiological characteristic data might be very closely related to the level of physical exertion, physical stress, or activity of the user; such physiological characteristic data may include, without limitation: heart rate data; respiration rate data; blood pressure data; perspiration data; blood glucose data; and the like.

After receipt at the set-top box device, at least some of the sensor data can be processed, analyzed, or otherwise handled in an appropriate manner (task 308). For example, the set-top box device might subject the raw sensor data to an amount of pre-processing, calibration, conditioning, filtering, or the like. For this exemplary embodiment, the set-top box device can be used to gather, organize, categorize, and/or format the raw sensor data for delivery to a remote subsystem, component, device, server, or service. Such pre-processing can be executed to transform raw sensor data (sent by the sensors) into a compatible format that can be understood by the set-top box device, by a network-based source or service, by a central processing server, or the like. Accordingly, the process 300 sends the raw or pre-processed sensor data to a remote system or service (task 310), using any suitable data communication technique or technology. In certain embodiments, the remote system could be a web-based content provider service having the necessary processing capability as described herein. In this regard, the remote system can receive the raw or pre-processed sensor data and perform additional processing and/or analysis on the received sensor data. As mentioned above, alternate embodiments might perform this additional sensor data processing at the set-top box device instead. In yet other embodiments, the sensor data processing could be distributed among the set-top box device, the remote system, and possibly other subsystems, devices, or components other than the set-top box device.

The sensor data is processed and analyzed in a suitable manner to determine a probable activity type, which is based upon or otherwise influenced by the raw sensor data (task 312). Accordingly, the process 300 uses the set-top box device to monitor the current physical activity level of the user and, in response thereto, determines or estimates the activity type, classification, form, or the like. Depending upon the particular deployment, any number of different probable activity types might be contemplated or considered by the system. In this regard, the set of probable activity types may include, without limitation, any of the following: a relatively low physical activity level; a relatively intermediate physical activity level; a relatively high physical activity level; tai chi activity; yoga activity; aerobic dance activity; kickboxing activity; boxing activity; exercise cycle activity; stair-stepper activity; Pilates activity; stretching activity; martial arts activity; meditation activity; calisthenics activity; walking activity; running activity; and the like. In practice, therefore, the sensor data can be analyzed and processed to enable the selection of at least one predefined probable activity type. Ideally, the available sensor data and the processing capability of the system will be sufficient to accurately determine a probable activity type that closely matches or accurately estimates the actual physical activity in which the user is currently engaged.

Referring again to FIG. 3, the process 300 may identify a content category that is correlated to the determined probable activity type (task 314). In other words, once a probable activity type has been selected, the process 300 can choose a classification, category, genre, set, or domain of available content that matches, fits, or is otherwise suitable for that probable activity type. In this regard, the identified content category may be associated with certain content characteristics such as, without limitation: audio/visual stimuli conveyed in the audio/video content; content genres; content volume characteristics; content tempo characteristics; content dynamic range characteristics; geographic/ethnic origin (e.g., Asian music, African music, Polish music); beat characteristics; beat intensity characteristics; musical key (e.g., major or minor); vocal type or characteristics (e.g., no vocals, male vocals only, female vocals only, chorus); and the like. For example, one content category may include dance music, while another content category might include classical music.

Another content category might include action and adventure movies, while a different content category might include nature videos with ambient and calm soundtracks. Yet another content category might include music or video content having relatively high dynamic range, while a different content category might include music or video content having relatively low dynamic range.

The process 300 may continue by selecting particular audio/video content from the identified category (task 316). The particular audio/video content is selected for playback and presentation to the user at the presentation device. Thus, the selected audio/video content will be correlated to the probable activity type, which in turn is influenced by the collected sensor data. Available audio/video content can be classified, identified, labeled, or tagged using any suitable technique or scheme for purposes of activity-based categorization. For example, content could be tagged with any number of fields that in turn could be used for activity-based categorization. These tagging fields may include, without limitation: beats per minute (BPM); genre; artist; song title; album title; movie title; actor name; year; tempo; dynamic range; and the like. In certain embodiments, the set-top box may analyze the received sensor data, determine the probable activity type, identify one or more tags that are appropriate for the probable activity type, and then send the identified tags to the network-based service for retrieval of matching audio/video content.

As one example, the system selects particular audio/video content having relatively high audio/visual stimuli when the probable activity type is indicative of relatively high physical activity, and selects particular audio/video content having relatively low audio/visual stimuli when the probable activity type is indicative of relatively low physical activity. As another example, the system selects particular audio/video content of a first genre (e.g., action, adventure, documentary, or talk show video content, or rock, classical, country, or jazz music content) when the probable activity type is indicative of relatively high physical activity, and selects particular audio/video content of a second genre when the probable activity type is indicative of relatively low physical activity. As yet another example, the system could select particular audio/video content having relatively high volume characteristics when the probable activity type is indicative of relatively high physical activity, and select particular audio/video content having relatively low volume characteristics when the probable activity type is indicative of relatively low physical activity. Moreover, the system could select particular audio/video content having relatively high tempo characteristics when the probable activity type is indicative of relatively high physical activity, and select particular audio/video content having relatively low tempo characteristics when the probable activity type is indicative of relatively low physical activity. As yet another non-limiting example, the system could select particular audio/video content having relatively high dynamic range characteristics when the probable activity type is indicative of relatively high physical activity, and select particular audio/video content having relatively low dynamic range characteristics when the probable activity type is indicative of relatively low physical activity.

It should be appreciated and understood that the particular audio/video content could be selected based on any number of other factors, considerations, preferences, etc. For example, the system could maintain preference data for the set-top box device and/or preference data for each individual user. Such preference data could be updated as needed (automatically or otherwise) so that the system selects content in a user-specific manner that is better customized to the likes and dislikes of the user. Preference data could indicate preferred genres, categories, artists, songs, movies, titles, and/or other identifiers, descriptors, tags, or labels.

It should be appreciated that, for this exemplary embodiment, most if not all of the sensor data processing is performed at a remote device or component. For instance, some or all of the sensor data processing might be performed by a network-based service, by a server system, at a headend facility, at a central control center, or the like. Alternatively, most if not all of the sensor data processing could be performed locally at the set-top box device (for example, sensor data processing could be executed by the sensor data processing module 212 shown in FIG. 2). In yet other embodiments, the sensor data processing could be distributed between the set-top box device and any number of other systems, devices, or components that are remote from the set-top box device.

Once the particular audio/video content has been selected, the process 300 provides the selected audio/video content to the set-top box device and/or to the presentation device as needed (task 318). Thus, the content presented by the presentation device can be automatically selected to match the current type or level of physical activity of the user. For the exemplary embodiment described here, the network-based source or service can be used to locate, identify, search for, or otherwise select URLs corresponding to web-based media content (e.g., streaming media files or downloadable media files) that matches the probable activity type. Thereafter, the network-based source or service can return one or more of those URLs to the set-top box device, which in turn can retrieve the corresponding content via a network such as the Internet. This scheme can be carried out if the set-top box device itself is web-enabled. This scheme allows much of the database-intensive processing to be offloaded from the set-top box device, and allows the system to leverage existing technologies that might be available via online services or websites (e.g., Internet radio services, web-based jukebox technologies, etc.). Use of network-based resources in this manner is desirable when dealing with extremely large libraries of content such as digital music, which might require significant database management capabilities.

In other embodiments, the selected audio/video content could be provided via traditional satellite or cable television switching and service delivery. In other words, the set-top box device can initiate switching of programming services as needed to accommodate the detected activity type. In layman's terms, this results in automatic "channel switching" to provide different audio/video content to the presentation device. In yet other embodiments, the selected audio/video content could be provided by accessing stored content on a storage media device or element, which may be resident at or coupled to the set-top box device. For example, task 318 may involve the operation of a DVR device or function that enables playback of stored content at the presentation device.

Moreover, in certain embodiments it may be desirable to control and/or initiate changes to certain presentation parameters or display characteristics (task 320), where such control is influenced by the probable activity type that was determined during task 312. For example, the set-top box device could initiate an adjustment of at least one setting of the presentation device that is currently being used to present the audio/video content to the user. The particular manner in which the system is automatically adjusted or modified may differ from one embodiment to another, and it may vary depending upon the analysis of the sensor data. For example, in certain scenarios it may be appropriate to adjust a brightness setting of a display being used to present the audio/video content to the user. As another example, it may be appropriate to adjust a volume setting of the presentation device currently being used to present the audio/video content to the user. As yet another example, it may be appropriate to adjust the playback speed of the particular audio/video content.

It may also be possible to initiate certain adjustments or commands for other household appliances, components, or features that need not be closely related to the presentation of the audio/video content itself. For example, depending upon the determined probable activity type, one or more of the following actions could be initiated, without limitation: dimming or turning off light fixtures; adjusting or turning off a heating or air conditioning system; pausing or turning off noisy household appliances such as washers or dryers; adjusting or turning off other presentation devices; adjusting or turning off other audio equipment; or the like. Such control actions may require some form of intercommunication between the set-top box device and the devices or system under its control (for example, a wireless home networking scheme might be appropriate). Moreover, any combination of the control, adjustment, changing, or modification approaches described above could be executed concurrently, sequentially, or otherwise to create a more comfortable exercise, meditation, or workout environment for the user.

Although not shown in FIG. 3, the process 300 may be designed to accommodate ongoing user feedback that can be used to enhance the content selection routine. Thus, after the process 300 provides the selected audio/video content to the presentation device, the user may be given the opportunity to indicate whether or not he or she likes or dislikes the content. The feedback could be more or less detailed, depending upon the embodiment. For example, the system could be configured to enable the user to provide feedback related to any number of different descriptors, tags, labels, or content identifiers. In this regard, the user might be able to indicate preferred (and/or not preferred) artists, genres, songs, albums, movie titles, actors, categories, and the like, using any type of scoring, ranking, or tagging scheme. Any feedback acquired by the system can thereafter be used to customize or modify the content selection scheme so that future selections are better suited to the user and/or to the different activity types handled by the system.

Although FIG. 3 depicts the process 300 exiting after task 320, in practice the process 300 could be performed in an ongoing manner. In this regard, the process 300 could be re-entered at an appropriate point after task 320 (or task 318) is performed. For example, the process 300 could be re-entered at task 306 to continue monitoring the current physical activity level of the user.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of presenting audio/video content to a user, the method comprising:
   receiving, with a set-top box device, first audio/video content provided by a network-based video services broadcasting system;
   operating the set-top box device to present the first audio/video content to the user;
   maintaining, with the set-top box device, a set of predefined probable activity types;
   monitoring, with the set-top box device, a physical activity level of the user;
   selecting, from the set of predefined probable activity types, a probable activity type based upon the monitored physical activity level, wherein the selected probable activity type estimates the monitored physical activity level of the user;
   selecting, with the set-top box device, second audio/video content provided by the network-based video services broadcasting system, the second audio/video content being categorized according to an amount of audio/visual stimuli conveyed in the second audio/video content, such that the amount of audio/visual stimuli is correlated to the selected probable activity type;
   switching programming services of the network-based video services broadcasting system to provide the second audio/video content to the user in place of the first audio/video content; and
   providing the second audio/video content to a presentation device.

2. The method of claim 1, wherein monitoring the physical activity level of the user comprises obtaining sensor data at the set-top box device, the sensor data being indicative of user activity.

3. The method of claim 1, wherein:
   the selecting step selects second audio/video content having relatively high audio/visual stimuli when the probable activity type is indicative of relatively high physical activity; and
   the selecting step selects second audio/video content having relatively low audio/visual stimuli when the probable activity type is indicative of relatively low physical activity.

4. The method of claim 1, wherein:
   the selecting step selects second audio/video content of a first genre when the probable activity type is indicative of relatively high physical activity; and
   the selecting step selects second audio/video content of a second genre when the probable activity type is indicative of relatively low physical activity.

5. The method of claim 1, wherein:
   the selecting step selects second audio/video content having relatively high volume characteristics when the probable activity type is indicative of relatively high physical activity; and
   the selecting step selects second audio/video content having relatively low volume characteristics when the probable activity type is indicative of relatively low physical activity.

6. The method of claim 1, wherein:
   the selecting step selects second audio/video content having relatively high tempo characteristics when the probable activity type is indicative of relatively high physical activity; and the selecting step selects second audio/video content having relatively low tempo characteristics when the probable activity type is indicative of relatively low physical activity.

7. The method of claim 1, wherein:
the selecting step selects second audio/video content having relatively high dynamic range characteristics when the probable activity type is indicative of relatively high physical activity; and
the selecting step selects second audio/video content having relatively low dynamic range characteristics when the probable activity type is indicative of relatively low physical activity.

8. The method of claim 1, further comprising controlling at least one presentation parameter associated with the second audio/video content, wherein the controlling is influenced by the probable activity type.

9. The method of claim 8, wherein the at least one presentation parameter comprises a parameter selected from the group consisting of: a brightness setting of the presentation device; a volume setting of the presentation device; and a playback speed of the second audio/video content.

10. A method of controlling presentation of content to a user, the method comprising:
maintaining a set of predefined probable activity types;
receiving, with a set-top box device, first audio/video content provided by a network-based video services broadcasting system;
operating the set-top box device to present the first audio/video content at a presentation device;
obtaining, at the set-top box device, sensor data that is indicative of physical activity of the user;
processing the sensor data to select, from the set of predefined probable activity types, a probable activity type for the user, wherein the selected probable activity type estimates the physical activity of the user;
identifying a category of audio/video content that is correlated to the selected probable activity type;
selecting, for playback at the presentation device, second audio/video content provided by the network-based video services broadcasting system, the second audio/video content being categorized to be included in the category;
switching programming services of the network-based video services broadcasting system to provide the second audio/video content to the user in place of the first audio/video content; and
operating the set-top box device to present the second audio/video content at the presentation device.

11. The method of claim 10, wherein the processing step is performed by the set-top box device.

12. The method of claim 10, wherein the processing step is performed by a system, device, or component other than the set-top device.

13. The method of claim 10, wherein the obtaining step obtains sensor data selected from the group consisting of: user motion data; user acceleration data; user velocity data; user posture data; user body position data; user heart rate data; user respiration data; user sound data; user perspiration data; user physiological characteristic data; and user temperature data.

14. A system for providing audio/video content to a user, the system comprising:
a set-top box device configured to provide audio/video content to a presentation device;
at least one sensor communicatively coupled to the set-top box device, the at least one sensor configured to provide sensor data to the set-top box device;
a sensor data processing module configured to process the sensor data to select, from a set of predefined probable activity types, a probable activity type for the user, wherein the selected probable activity type estimates whether the user is currently engaged in relatively low physical activity or relatively high physical activity; and
a controller coupled to the sensor data processing module, the controller configured to operate the set-top box device to receive first audio/video content from a network-based video services broadcasting system, and to present the first audio/video content at the presentation device, and the controller further configured to select second audio/video content provided by the network-based video services broadcasting system for playback at the presentation device, the second audio/video content having an amount of audio/visual stimuli that is correlated to the probable activity type, wherein the second audio/video content has relatively low audio/visual stimuli when the selected probable activity type is indicative of relatively low physical activity of the user, and wherein the second audio/video content has relatively high audio/visual stimuli when the selected probable activity type is indicative of relatively high physical activity of the user, and the controller further configured to switch programming services of the network-based video services broadcasting system and operate the set-top box device to present the second audio/video content at the presentation device in place of the first audio/video content.

15. The system of claim 14, wherein the at least one sensor comprises a sensor selected from the group consisting of: a motion detector; an accelerometer; a pedometer; a perspiration meter; a video camera; a still camera; a microphone; a sound meter; a physiological characteristic sensor; and a thermometer.

16. The system of claim 14, wherein the sensor data processing module is implemented in a subsystem, device, or component other than the set-top box device.

17. The system of claim 16, wherein the sensor data processing module is maintained by a network-based content provider.

18. The system of claim 14, wherein the controller is implemented in a subsystem, device, or component other than the set-top box device.

19. The system of claim 14, wherein the controller is configured to:
identify a category of audio/video content that is correlated to the probable activity type; and
select the second audio/video content from the identified category.

20. The system of claim 19, wherein the category is associated with variable content characteristics, the variable content characteristics selected from the group consisting of: audio/visual stimuli conveyed in the audio/video content; content genres; content volume characteristics; content tempo characteristics; geographic/ethnic origin; beat characteristics; beat intensity characteristics; musical key; vocal type or characteristics; and content dynamic range characteristics.

* * * * *